(12) United States Patent
Ozer

(10) Patent No.: US 8,639,445 B2
(45) Date of Patent: Jan. 28, 2014

(54) IDENTIFICATION OF RELATED RESIDUES IN BIOMOLECULAR SEQUENCES BY MULTIPLE SEQUENCE ALIGNMENT AND PHYLOGENETIC ANALYSIS

(75) Inventor: Stuart Ozer, Moraga, CA (US)

(73) Assignee: Microsoft Corporation, Redmond, WA (US)

( * ) Notice: Subject to any disclaimer, the term of this patent is extended or adjusted under 35 U.S.C. 154(b) by 349 days.

(21) Appl. No.: 11/781,920

(22) Filed: Jul. 23, 2007

(65) Prior Publication Data

US 2009/0030925 A1 Jan. 29, 2009

(51) Int. Cl.
G06F 19/22 (2011.01)
G06F 19/14 (2011.01)
G06F 19/24 (2011.01)

(52) U.S. Cl.
CPC ............. G06F 19/22 (2013.01); G06F 19/14 (2013.01); G06F 19/24 (2013.01)
USPC .......................................................... 702/19

(58) Field of Classification Search
CPC .......... G06F 19/14; G06F 19/22; G06F 19/24
USPC .......................................................... 702/19
See application file for complete search history.

(56) References Cited

U.S. PATENT DOCUMENTS

| 5,270,163 A | 12/1993 | Gold et al. |
| 5,496,938 A | 3/1996 | Gold et al. |
| 5,738,990 A | 4/1998 | Edwards et al. |
| 6,231,812 B1 | 5/2001 | Rothberg et al. |
| 6,377,893 B1 | 4/2002 | Benner |
| 6,451,524 B1 | 9/2002 | Ecker |
| 6,564,151 B1 | 5/2003 | Pellegrini et al. |
| 2003/0149537 A1 | 8/2003 | Binkowski et al. |
| 2004/0204861 A1 | 10/2004 | Benner |
| 2005/0084907 A1 | 4/2005 | Fox |

OTHER PUBLICATIONS

Black, PE and Algorithms and Theory of Computation Handbook, CRC Press LLC, 1999, "tree", in Dictionary of Algorithms and Data Structures [online], Paul E. Black, ed., U.S. National Institute of Standards and Technology. Aug. 14, 2008.*
Yang, Z., Kumar, S. & Nei, M. A new method of inference of ancestral nucleotide and amino acid sequences. Genetics 141, 1641-1650 (1995).*
Giribet, G. & Wheeler, W. C. on gaps. Molecular Phylogenetics and Evolution 13, 132-143 (1999).*
Fitch, W. M. Toward defining the course of evolution: Minimum change for a specific tree topology. Systematic Zoology 20, 406-416 (1971).*
Hartigan, J. A. Minimum mutation fits to a given tree. Biometrics 29, 53-65 (1973).*

(Continued)

Primary Examiner — Soren Harward
(74) Attorney, Agent, or Firm — Lee & Hayes, PLLC

(57) ABSTRACT

Data clustering is described for determining related components of the data. In one example, information on biomolecules may be clustered into groups in which the biomolecular data in a clustered group may indicate data that shares a relationship. For example, monomers of a protein molecule or a nucleic acid molecule may be mapped to an evolutionary or phylogenetic tree. Candidate groupings of the information may be obtained based on evolutionary relationships among sequences corresponding to the molecules.

25 Claims, 8 Drawing Sheets

(56) References Cited

OTHER PUBLICATIONS

Allman, E. S. & Rhodes, J. A. Lecture notes: The mathematics of phylogenetics. Tech. Rep., IAS/Park City Mathematics Institute, Park City, UT (2005).*

Kimelman, D., Leban, B., Roth, T. & Zernik, D. Reduction of visual complexity in dynamic graphs. In Goos, G., Hartmanis, J., van Leeuwen, J., Tamassia, R. & Tollis, I. G. (eds.) DIMAS International Workshop, GD '94, 218-225 (Springer, 1994).*

Shindyalov, I. N., Kolchanov, N. A. & Sander, C. Can three-dimensional contacts in protein structures be predicted by analysis of correlated mutations? Protein Eng. 7, 349-358 (1994).*

Thomas, J. W. et al. Comparative analyses of multi-species sequences from targeted genomic regions. Nature 424, 788-793 (2003).*

Cooper, G. M. et al. Quantitative estimates of sequence divergence for comparative analyses of mammalian genomes. Genome Research 13, 813-820 (2003).*

Valdar, W. S. Scoring residue conservation. Proteins 48, 227-241 (2002).*

Castresana, J. Selection of conserved blocks from multiple alignments for their use in phylogenetic analysis. Molecular Biology and Evolution 17, 540-552 (2000).*

Taylor, W. R. & Hatrick, K. Compensating changes in protein multiple sequence alignments. Protein Engineering, Design and Selection 7, 341-348 (1994).*

Zwickl, D. J. & Hillis, D. M. Increased taxon sampling greatly reduces phylogenetic error. Systematic Biology 51, 588-598 (2002).*

Hein, J. A new method that simultaneously aligns and reconstructs ancestral sequences for any number of homologous sequences, when the phylogeny is given. Molecular Biology and Evolution 6, 649-668 (1989).*

Giancarlo Mauri et al. "Algorithms for Pattern Matching and Discovery in RNA Secondary Structure", Theoretical Computer Science, May 2005, vol. 335, Issue 1.

Liu J. et al. "A Method for Aligning RNA Secondary Structures and its Application to RNA Motif Detection", BMC Bioinformatics. 2005.

"The Alignment", This text is modified from: Larsen N. and Zwieb C. SRP-RNA Sequence Alignment and Secondary Structure Nucleic Acids Research, vol. 19, No. 2, 209-215 (1990), Updated Jul. 5, 2006.

Ying Xu et al. "Exact pattern matching for RNA secondary structures", ACM International Conference Proceeding Series; vol. 55, Proceedings of the second conference on Asia-Pacific bioinformatics—vol. 29, 2004.

* cited by examiner

IDENTIFICATION OF RELATED RESIDUES IN BIOMOLECULAR SEQUENCES BY MULTIPLE SEQUENCE ALIGNMENT AND PHYLOGENETIC ANALYSIS

BACKGROUND

Biomolecules are composed of monomers in which one or more monomers may share a relationship with another monomer. For example, a protein molecule or polypeptide may be composed of any number or type of amino acid residues linked in a polypeptide chain in a particular sequence. Some of the amino acid residues in the molecule may be related to other amino acid residues either in the same molecule or in another molecule with which it interacts.

Similarly, other biomolecules, such as nucleic acid molecules also contain different monomers—in this case consisting of nucleotides—of which some may be related to others. The relationship of such monomers in a biomolecule may include, for example, a structural relationship or a functional relationship.

Efficient and accurate identification of related groups of monomers of biomolecular sequences is important in achieving biotechnological advances in research and development. However, there is currently no efficient method for determining groupings of monomers in a biomolecular sequence, or among related interacting sequences.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one example, a method is described in which clustering patterns of biomolecular sequences or molecules may be generated. Any number of sequences, representing the same functional molecule or set of molecules from any number of different species may be aligned and/or mapped to an evolutionary or phylogenetic tree. Different monomers, such as amino acids or nucleotides, of the biomolecular sequence may be clustered or grouped together. In one example, clustering may be based on evolutionary events such as event counts or sequence counts across different sequences at different positions. The different sequences may represent any number of different species in an evolutionary tree.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples. Systems described herein are provided as examples and not limitations. As those skilled in the art will appreciate, the present examples are suitable for application in a variety of different types of computing systems.

Figure 1:
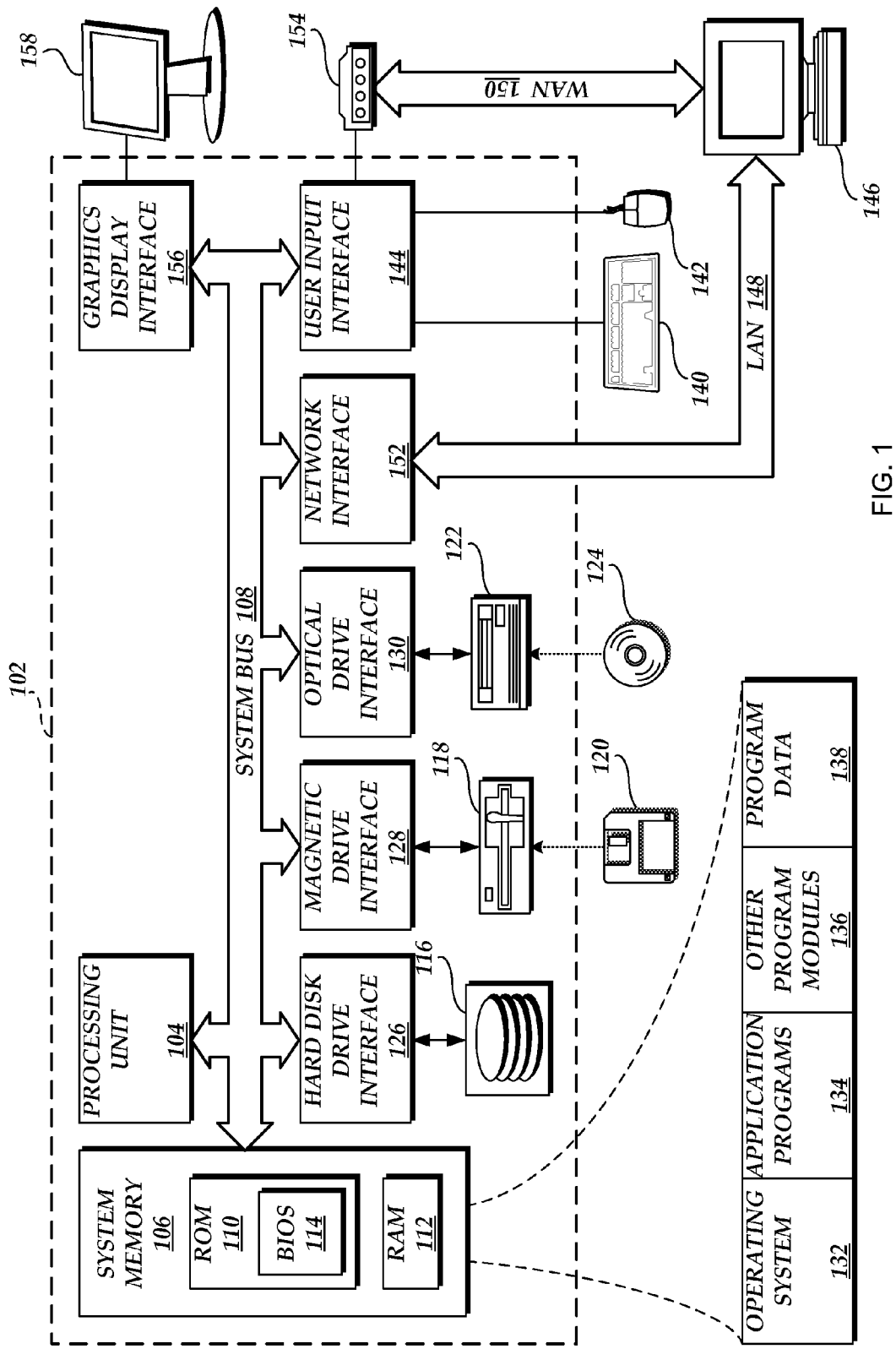
FIG. 1 illustrates an example of a suitable computing system environment.

FIG. 1 illustrates an example of a suitable computing system environment or architecture in which computing subsystems may provide processing functionality. The computing system environment is only one example of a suitable computing environment and is not intended to suggest any limitation as to the scope of use or functionality of the invention. Neither should the computing environment be interpreted as having any dependency or requirement relating to any one or combination of components illustrated in the exemplary operating environment.

The method or system disclosed herein is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The method or system may be described in the general context of computer-executable instructions, such as program modules, being executed by a computer. Generally, program modules include routines, programs, objects, components, data structures, etc. that perform particular tasks or implement particular abstract data types. The method or system may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the method or system includes a general purpose computing device in the form of a computer 102. Components of computer 102 may include, but are not limited to, a processing unit 104, a system memory 106, and a system bus 108 that couples various system components including the system memory to the processing unit 104. The system bus 108 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 102 typically includes a variety of computer readable media. Computer readable media can be any available media that can be accessed by computer 102 and includes both volatile and nonvolatile media, removable and non-removable media. By way of example, and not limitation, computer readable media may comprise computer storage media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 102. Combinations of the any of the above should also be included within the scope of computer readable storage media.

The system memory 106 includes computer storage media in the form of volatile and/or nonvolatile memory such as read only memory (ROM) 110 and random access memory (RAM) 112. A basic input/output system 114 (BIOS), containing the basic routines that help to transfer information between elements within computer 102, such as during start-up, is typically stored in ROM 110. RAM 112 typically contains data and/or program modules that are immediately accessible to and/or presently being operated on by processing unit 104. By way of example, and not limitation, FIG. 1 illustrates operating system 132, application programs 134, other program modules 136, and program data 138.

The computer 102 may also include other removable/non-removable, volatile/nonvolatile computer storage media. By way of example only, FIG. 1 illustrates a hard disk drive 116 that reads from or writes to non-removable, nonvolatile magnetic media, a magnetic disk drive 118 that reads from or writes to a removable, nonvolatile magnetic disk 120, and an optical disk drive 122 that reads from or writes to a removable, nonvolatile optical disk 124 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 116 is typically connected to the system bus 108 through a non-removable memory interface such as interface 126, and magnetic disk drive 118 and optical disk drive 122 are typically connected to the system bus 108 by a removable memory interface, such as interface 128 or 130.

The drives and their associated computer storage media discussed above and illustrated in FIG. 1, provide storage of computer readable instructions, data structures, program modules and other data for the computer 102. In FIG. 1, for example, hard disk drive 116 is illustrated as storing operating system 132, application programs 134, other program modules 136, and program data 138. Note that these components can either be the same as or different from additional operating systems, application programs, other program modules, and program data, for example, different copies of any of the elements. A user may enter commands and information into the computer 102 through input devices such as a keyboard 140 and pointing device 142, commonly referred to as a mouse, trackball or touch pad. Other input devices (not shown) may include a microphone, joystick, game pad, pen, scanner, or the like. These and other input devices are often connected to the processing unit 104 through a user input interface 144 that is coupled to the system bus, but may be connected by other interface and bus structures, such as a parallel port, game port or a universal serial bus (USB). A monitor 158 or other type of display device is also connected to the system bus 108 via an interface, such as a video interface or graphics display interface 156. In addition to the monitor 158, computers may also include other peripheral output devices such as speakers (not shown) and printer (not shown), which may be connected through an output peripheral interface (not shown).

The computer 102 may operate in a networked environment using logical connections to one or more remote computers, such as a remote computer. The remote computer may be a personal computer, a server, a router, a network PC, a peer device or other common network node, and typically includes many or all of the elements described above relative to the computer 102. The logical connections depicted in FIG. 1 include a local area network (LAN) 148 and a wide area network (WAN) 150, but may also include other networks. Such networking environments are commonplace in offices, enterprise-wide computer networks, intranets and the Internet.

When used in a LAN networking environment, the computer 102 is connected to the LAN 148 through a network interface or adapter 152. When used in a WAN networking environment, the computer 102 typically includes a modem 154 or other means for establishing communications over the WAN 150, such as the Internet. The modem 154, which may be internal or external, may be connected to the system bus 108 via the user input interface 144, or other appropriate mechanism. In a networked environment, program modules depicted relative to the computer 102, or portions thereof, may be stored in the remote memory storage device. By way of example, and not limitation, remote application programs may reside on a memory device. It will be appreciated that the network connections shown are exemplary and other means of establishing a communications link between the computers may be used.

Biomolecules may be analyzed to determine portions of the biomolecule that may interact or share a relationship with other portions of either the same or other biomolecules. In one example, a computer system as described above may be used to analyze biomolecules. Biomolecules include molecules that may be found in cells of living organisms. For example, biomolecules may include nucleic acid molecules such as various types of ribonucleic acid (RNA), as well as proteins. The molecules to be analyzed contain a sequence of monomers composed of either nucleotides (in the case of nucleic acids) or amino acids (in the case of proteins). For example, a nucleic acid molecule such as Ribosomal RNA (rRNA) from a particular organism is composed of a specific combination of nucleotides linked together in a sequence. The nucleotides that compose any ribonucleic acid molecule (RNA) may be selected from the nucleotide monomers adenosine (A), guanine (G), cytosine (C), or uracil (U). Likewise, a deoxriboynucleic acid molecule (DNA) may contain a sequence of nucleotides selected from adenosine (A), guanine (G), cytosine (C), or thymine (T).

Biomolecules may also include protein molecules that may include any number or type of amino acid residues linked in a specific sequence or primary structure. In addition to specific sequences of monomers such as nucleotides in nucleic acids or amino acids in proteins, biomolecules may also display additional structural characteristics. For example, a protein may form any number of secondary structures and may also be folded in any number of ways to form tertiary structures. In one example, folding of the protein or polypeptide in various complex configurations may form a particular spatial relationship among certain portions of the protein. The spatial relationship may be characterized by the tertiary structure of the protein. In addition, any number or type of proteins may interact with other proteins. The inter-molecular interaction may form additional structural characteristics (e.g., quarternary structure). Hence, different portions of the protein or polypeptide may share a relationship or may share a relationship with other proteins or biomolecules. Knowledge of the form or type of relationship including which amino acids or which subunits of the molecule are involved in the relationship may affect many aspects of molecular research. For example, protein function or drug design may be associated with such intra- and/or inter-molecular relationships.

Similarly, nucleic acid molecules (e.g., RNA) may also contain monomers that may be related to other monomers. As with proteins, RNA molecules such as Ribosomal RNA (rRNA) may form secondary and tertiary structures as individual monomers (nucleotides) form linkages with other monomers that are not immediately adjacent in sequence. The related monomers (e.g., nucleotides) may be located proximate to each other or may be located distant from each other in sequence. In one example, a method is described for identifying related monomers of biomolecules. For example, related monomers of biomolecules may be clustered based on evolutionary or phylogenetic variation patterns as described in more detail below.

Figure 2:
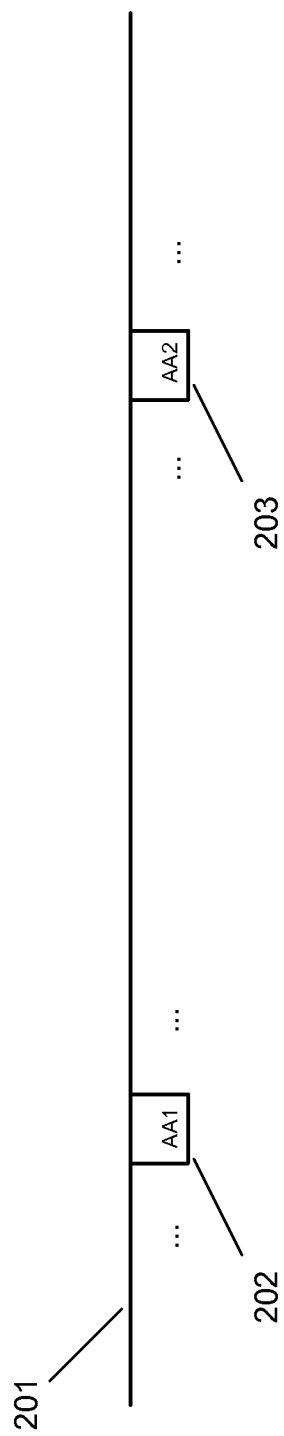
FIG. 2 illustrates one example of a polypeptide containing amino acid residues.

FIG. 2 illustrates one example of a polypeptide containing amino acid residues. In this example, two amino acid residues (202, 203) are illustrated schematically in a polypeptide 201, however, the polypeptide 201 may contain any number of amino acids. Also illustrated in the example of FIG. 2, amino acid 202 and amino acid 203 may be located at any distance from each other within the sequence.

Figure 3:
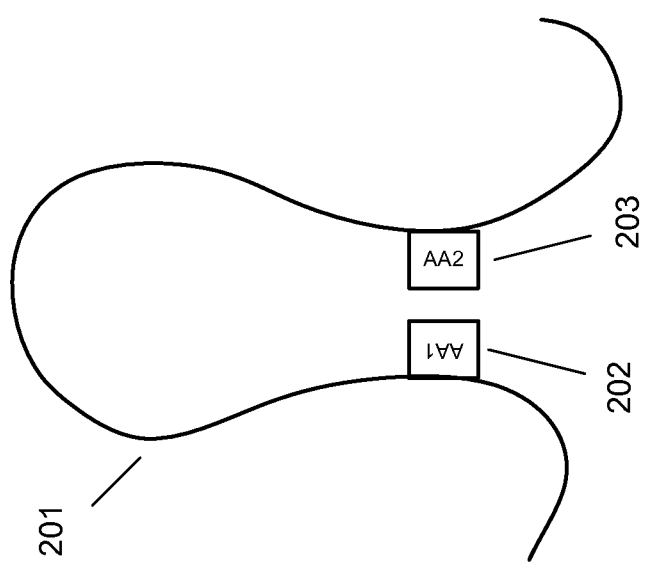
FIG. 3 illustrates a polypeptide folded into a tertiary structure.

FIG. 3 illustrates the polypeptide of FIG. 2 folded upon itself forming a tertiary structure. In this case, amino acid 202 and amino acid 203 are spatially located in proximity to each other. Also in this example, modifications in either amino acid 202 or amino acid 203 may affect the other amino acid. For example, a modification in amino acid 202 may result in a change in amino acid 203. Conversely, a modification in amino acid 203 may result in a change in amino acid 202. Thus, a relationship may exist between the two amino acids.

Figure 4:
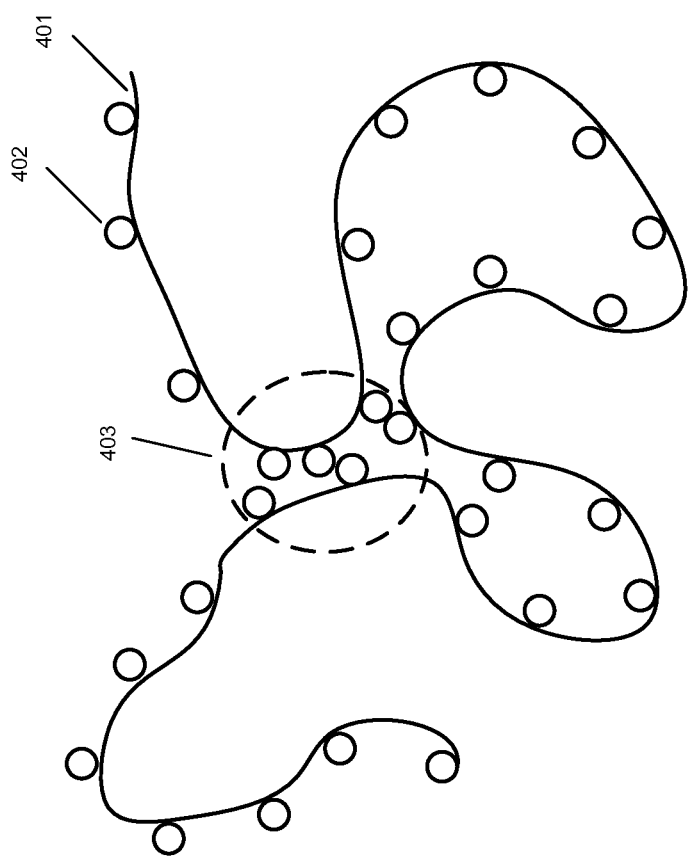
FIG. 4 is a schematic illustrating an example of a nucleic acid molecule.

FIG. 4 illustrates an example of a nucleic acid molecule 401 containing any number of nucleotides 402. The structure of the nucleic acid molecule 401 in this example includes a portion of the molecule in which a portion folds upon another portion of the molecule (e.g., area 403). In area 403 of the nucleic acid molecule 401, several nucleotides of the nucleic acid molecule share a relationship. The relationship may result from any number of factors. For example, the relationship may result from relative locations of the nucleotides, functional relationships, relative charges, etc. In this example, area 403 contains nucleotides that are linked such that changes to any of the nucleotides in the area 403 may result in a stabilizing change in one or more nucleotides in area 403.

In one example, sequence analysis may be performed on a biomolecule such as nucleic acid molecules or protein or polypeptide molecules to determine the sequence of monomers in the molecule. In the case of a polypeptide, the sequence of amino acid residues in the polypeptide may be determined from a variety of different species. Each of the polypeptide sequences from the different species may be aligned to determine corresponding positions in the polypeptide sequences across the different species. The different species may include, for example, different organisms that may be related to each other in an evolutionary sense. An evolutionary tree (e.g., phylogenetic tree) may be created based on relationships of the different species. Also, the polypeptide sequences (or nucleic acid sequences) may be mapped to the evolutionary tree.

Figure 5:
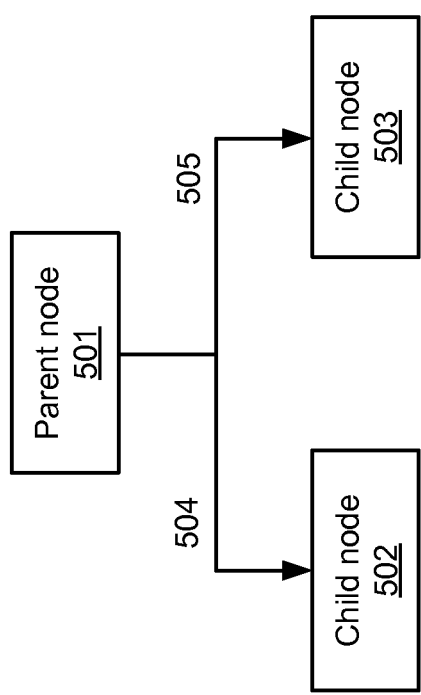
FIG. 5 illustrates an example of an evolutionary tree.

The evolutionary tree may contain any number of branches and nodes based on the related species included in the tree. A node in the tree may represent, for example, a sequence (e.g., nucleic acid or protein) from a particular organism or species of organism. Branches of the tree may indicate different evolutionary pathways from the node. For example, a sequence of a first node may be related to a sequence of a child node where the child node may represent a descendent of the first node. FIG. 5 illustrates an example of an evolutionary tree containing nodes representing sequences (e.g., nucleic acid or protein/polypeptide). The sequence of a node may be associated with a particular organism or species. As FIG. 5 illustrates, a parent node 501 may be associated with a corresponding nucleic acid molecule or protein molecule. The parent node 501 may further represent a species or organism. Also illustrated in FIG. 5, a child node may be related to the parent node 501. The child node may represent a species that is a descendent of the parent node. In this case, two child nodes (502, 503) are illustrated although any number or type of child nodes may be present. Also, any child node may have additional associated child nodes below the child node (not shown).

Also illustrated in FIG. 5 are branches in the evolutionary tree. The branches (504, 505) represent pathways from a parent node 501 to child nodes (502, 503). Hence, evolutionary events may occur to cause a change from a sequence associated with parent node 501 to any of the child nodes 502, 503. Such changes may include any type of change in the sequence including point mutations of monomers (e.g., nucleotides or amino acids) and/or corresponding changes in other monomers of the sequence that have a relationship with the monomer undergoing a mutation or other change.

In another example, a method and system is described for computing candidate groupings of monomers in a sequence. The monomers included in a grouping may include any number of monomers that may undergo change that is related to changes in other monomers in the group. Hence, the monomers in a grouping may be related in some way such as functionally or structurally.

In this example, a monomer of a sequence corresponds to a particular position within the sequence. For example, a particular cytosine nucleotide in a nucleic acid sequence corresponds to the particular position in the sequence occupied by the nucleotide. The position in the sequence associated with this nucleotide may further be related (e.g., functionally or structurally) with a position (or monomer) at another location in the sequence. Hence, any position in the sequence may share a relationship with another position in the sequence. Also, the related positions in the sequence may be located at any relative location with respect to each other. In addition, any number of positions may be associated with any number of other positions in a sequence. Thus, any number of positions in a sequence may be related to any number of other positions in the sequence.

Figure 6:
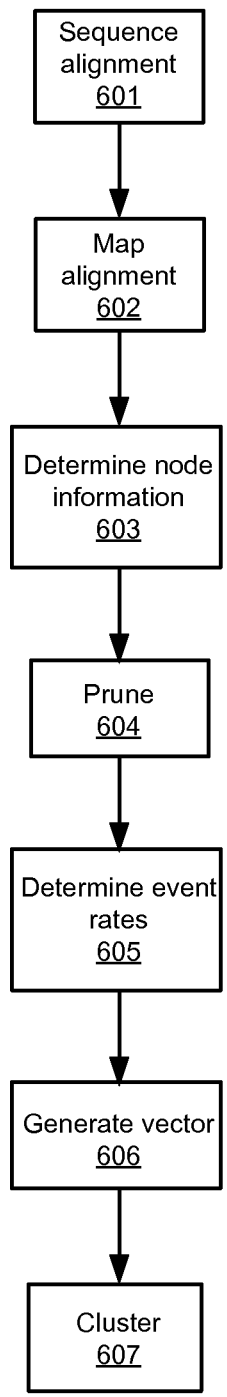
FIG. 6 is a flowchart illustrating one example of clustering positions or monomers of a sequence.

FIG. 6 is a flowchart illustrating one example of clustering positions or monomers of a sequence. In STEP 601, sequences corresponding to a molecule from different species may be aligned. For example, a particular protein or nucleic acid molecule may be obtained from a number of diverse species and may further be aligned with each other. The sequences may be organized based on, for example, a species corresponding to the sequences or a relationship between the corresponding species. For example, in STEP 602, the sequences may be mapped to an evolutionary tree based on the species corresponding to each of the sequences. In this example, a node may include any number of sequences for a species and may further have any number or type of child nodes (e.g., descendent species). In addition, a species at a node may not have any descendents.

In STEP 603, information at any given node may be determined. In some cases, parent nodes may corresponding to existing species or existing sequences. In other cases, parent nodes may represent implied ancestral species that do not exist for which event counts may be obtained. The event counts for the "empty" parent nodes may be based, for example, in the composition of children nodes with respect to the parent node. In another example, the information may pertain to evolutionary events associated with the species and/or sequences corresponding to the species. Also, the information may include an event count corresponding to a node or sequence or a sequence count. For example, a position within a sequence may be identified at a first node. In addition, a corresponding position may be identified at a child node, the child node being a descendent of the first node. The position in each of the sequences may be compared to determine if a change has occurred between the sequence of the first node and the sequence of the descendent or child node. In addition, the child node may have any number of child nodes (i.e., second generation nodes that are descendent nodes of the first node). Any of the second generation child nodes may contain a corresponding position in the respective sequences. The second generation child node sequences may be analyzed to determine a number of additional changes at the corresponding position to generate an event count. The event count may represent, in this example, a number of times that a position in a sequence of a node changes at any child node that is a descendent of the node. The event count may be generated in any number of ways and the present description is not limited to any particular method. For example, the event count may be determined by applying a recursive technique. Such recursive techniques may be applied for binary phylogenetic trees or evolutionary trees or may be further adapted to be applied to non-binary phylogenetic/evolutionary trees. In another example, a Fitch algorithm may be applied to generate the event count.

The process may be performed for any number of positions within the sequence of any given node. For example, an event count may be generated for each position within a sequence corresponding to a node. Thus, each position in the sequence may be compared to corresponding positions at each of the child nodes below the parent node in the evolutionary tree and an event count identifying the number of times the corresponding position changes in each of the child nodes may be generated. In addition, the process may be repeated for any node. In one example, the process is repeated for each position in each sequence at each node. Hence, a plurality of event counts may be generated for each position of each sequence at each node where the event counts each describe the number of changes at a respective position within a sequence at a node as compared to a corresponding position at each child node with respect to the parent node.

Also in this example, any number of child nodes may contain sequences that have a position corresponding to the position in the sequence of a parent node but any number of child nodes may not contain a corresponding position in a corresponding sequence. For example, a sequence count may be determined for describing a number of child sequences containing a position of interest. In this example, a parent node may have any number of child nodes at any number of different levels within the evolutionary tree. A sequence corresponding to the parent node may contain a particular position of which certain child nodes contain a corresponding position and certain other child nodes do not contain the corresponding position. The sequence count may be determined indicating the number of sequences in child nodes descendent from the parent node containing a position corresponding to a particular position in the sequence of the parent node.

In yet another example, a species count may be determined for describing the number of species associated with sequences in child nodes. For example, a parent node may have an associated sequence that contains a particular position. Any number of sequences corresponding to child nodes of the parent node may contain a corresponding position. Also, the sequences of the child nodes may be associated with any number of species which may be descended from the species corresponding to the parent node of the evolutionary tree. A species count may be determined for identifying a number of species associated with sequences at a node or at any child node below the node for each position in the sequence.

In STEP 604, the evolutionary tree may be "pruned" such that nodes in the evolutionary tree may contain sequences associated with a certain number of species. For example, a certain minimum number of species for a given node may be determined and the evolutionary tree may be pruned so that each node contains at least the determined minimum number of species.

Figure 7:
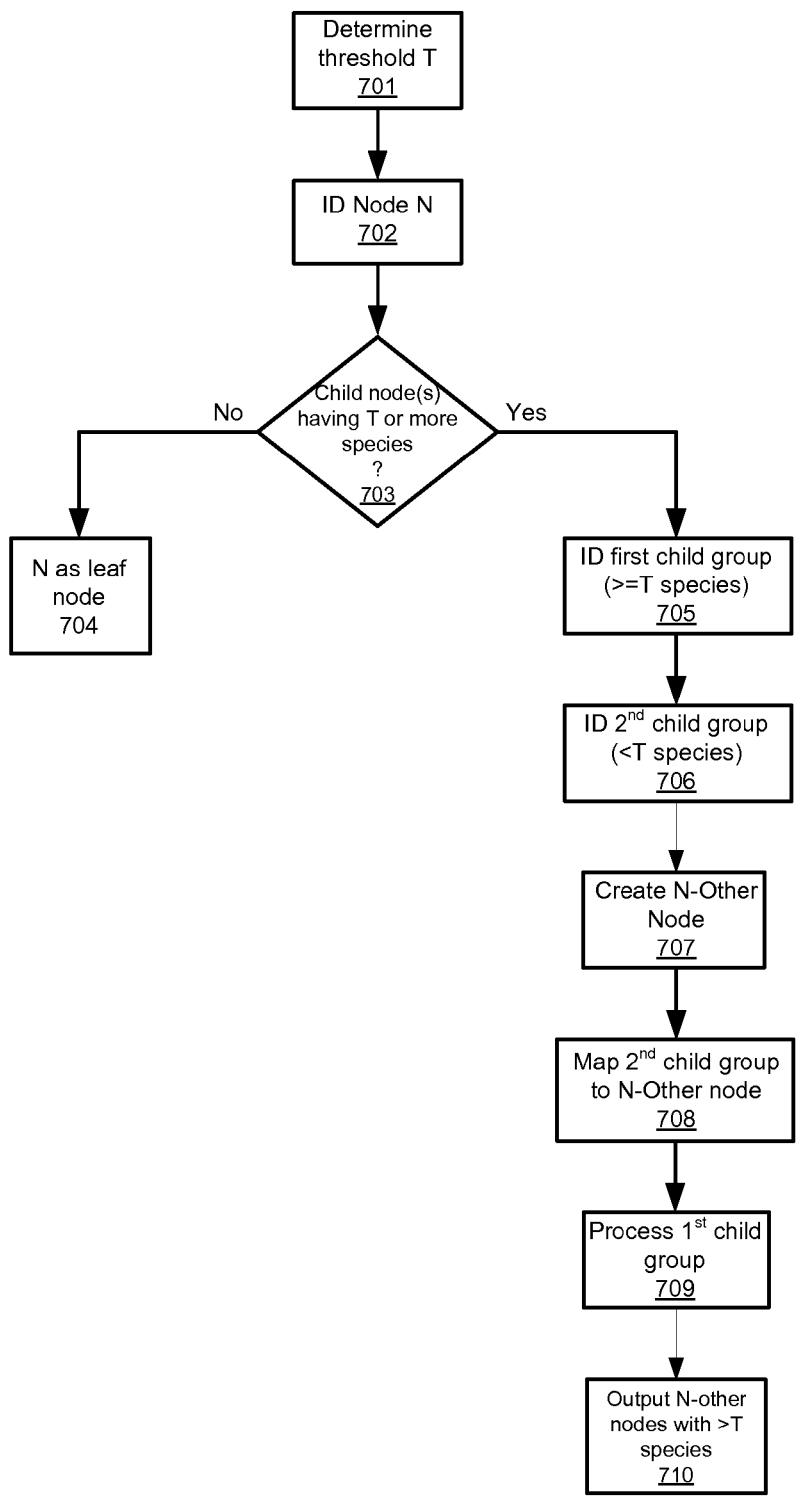
FIG. 7 is a flowchart illustrating one example of pruning an evolutionary tree.

In one example of pruning the evolutionary tree, siblings below a predetermined threshold may be removed. FIG. 7 is a flowchart illustrating one example for pruning a phylogenetic or evolutionary tree. In this example, a threshold T may be determined for aggregating siblings (STEP 701). The threshold T may indicate a minimum number of descendent species for a node. If a node does not contain at least the minimum number of T species, the node may be removed or pruned from the evolutionary tree. The process may be repeated for any number of nodes in the tree. In one example, the process is repeated for all nodes in a given tree. As the example of FIG. 7 illustrates, node N is selected for potential pruning (STEP 702). The node N selected may be located at a root of the tree and iterations of the process with additional nodes in the tree may progress outward from the root of the tree. Each of the child nodes C that descend from node N are examined to determine a number of species associated with each of the child nodes C (STEP 703). If none of the child nodes C of node N contain the minimum threshold T of species ("No" branch of STEP 703), node N may be identified as a leaf node (STEP 704). The next node N may then be evaluated in similar fashion.

If at least one child node C of node N contains the minimum threshold T of species ("Yes" branch of STEP 703), each of the child nodes C of node N may be identified based on relative numbers of associated species for each of the child nodes. In this example, a first child group may be identified (STEP 705) where each of the child nodes C in the first child group contains at least the minimum number T species. Also, a second child group may be identified (STEP 706) where each of the child nodes C in the second child group contain less than the minimum number T species.

In STEP 707, a new temporary or combination node is created (e.g., "N-Other Node" in this example). The child nodes of the second child group (i.e., the child nodes C of node N that contain less than the minimum number T species) are mapped to the N-Other node or combination node (STEP 708). In STEP 708, mapping may be accomplished in a variety of ways. For example, mapping may include identifying corresponding event counts and summing the identified event counts for each of the child nodes C in the second child group. The resulting summed event count may be assigned to the N-Other Node or combination node. Similarly, sequence counts for each of the child nodes C in the second child group may also be summed and assigned to the N-Other Node or combination node. Any relevant characteristic or parameter of the child nodes in the second child group may be similarly mapped to the N-Other Node or combination node.

In STEP 709, the child nodes C in the first child group are processed. Each of the child nodes C in the first child group may be processed in a similar manner as node N. For example, a child node from the first child group may have any number of child nodes itself (C' child nodes). The C' child nodes may be identified in a first group of C' child nodes that contain at least the minimum number T species or in a second group of C' child nodes that contain less than the minimum number T species. As described above, additional nodes may be created and C' child nodes containing at least the minimum number T species may be mapped to the additionally created node. This process may be repeated any number of times with any number of nodes. For example, the process may be repeated for all of the remaining nodes in the tree.

In STEP 710, each of the nodes may be determined has having at least the minimum number T species or containing less than the minimum number T species. Each of the nodes (e.g., the created nodes to which child nodes have been mapped) containing less than the minimum number T species may be discarded in this example. The remaining non-discarded nodes contain at least the minimum number T species and may be output to provide a set of leaf nodes containing counts of evolutionary events of at least a minimum size (i.e., T).

Figure 8:
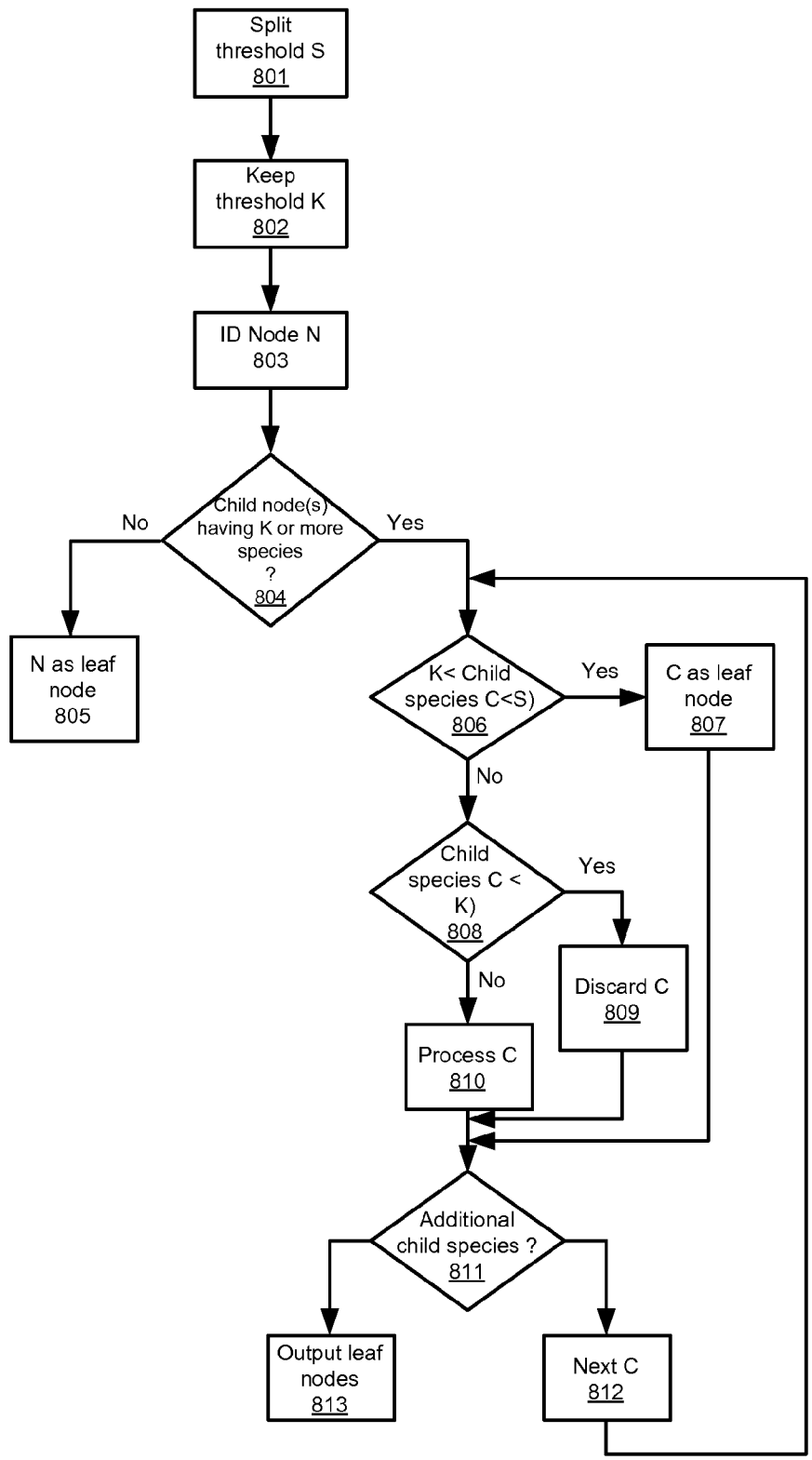
FIG. 8 is a flowchart illustrating another example of pruning an evolutionary tree.

In another example of pruning the evolutionary tree, multiple thresholds may be identified. FIG. 8 is a flowchart illustrating another example of pruning an evolutionary tree. In this example, two thresholds are identified for determining processing of a node. A first threshold (e.g., split threshold S) may be determined (STEP 801) for indicating a node that may potentially be divided into multiple nodes. A second threshold (e.g., keep threshold K) may be determined (STEP 802) for indicating whether a node may be maintained in the tree or may be discarded from the tree. Hence, in this example, the thresholds (S and/or K, where S is greater than K) may indicate a number of species that a particular node may have. The process as described below may be repeated any number of times recursively for any number of nodes in the tree. In one example, all of the nodes in the tree are processed.

In STEP 803, a node N in the tree is identified for processing. Node N may be selected at a root of the tree and the process may be repeated subsequently for additional nodes proceeding toward the leaves of the tree. Any node N may have any number or type of associated child nodes C that descend from node N. Each of the child nodes C of node N may be analyzed to determine a number of species associated with each of the child nodes C (STEP 804). If each of the child nodes C of node N contain less than the second threshold K, the node N may be identified as a leaf node (STEP 805). The process may be repeated with a next node.

If at least one of the child nodes C contain at least a minimum number K species ("Yes" branch of STEP 804), the number of descendent species corresponding to each of the child nodes C may be identified. For example, a number of descendent species associated with a first child node C may be identified. If the number of descendent species for the child node C is greater than the minimum number K species but less than or equal to the maximum number S species ("Yes" branch of STEP 806), then the child node C may be identified as a leaf node (STEP 807). If the number of descendent species for the child node C is less than the minimum number K species ("Yes" branch of STEP 808), then the child node C may be discarded (STEP 809). Otherwise, the child node C has greater than the maximum number S species (STEP 810) and the child node may be further processed.

In STEP 810, when the child node C has greater than the maximum number S descendent species, the process may be applied iterative or recursively to the child node C. For example, all of the direct child nodes C' of child node C may be identified. If none of child nodes C' contain at least the minimum number K descendent species, then child node C may be identified as a leaf node. If at least one of child nodes C' contain at least the minimum number K descendent species, then the number of descendent species associated with each of the child nodes C' may be identified. Each child node C' containing less than the minimum number K descendent species may be discarded, each child node C' containing greater than (or equal to) the minimum number K descendent species but less than (or equal to) the maximum number S descendent species, the child node C' may be identified as a leaf node. Any child node C' containing greater than the maximum number S descendent species may be further processed as described.

The process may be repeated for each of the child nodes C (STEP 811). If additional child nodes C exist ("Yes" branch of STEP 811), then the next child node C is evaluated in a similar fashion (STEP 812). If the process is complete, for example, no additional child nodes exist and/or all nodes in the tree have been analyzed ("No" branch of STEP 811), then the identified leaf nodes may be output or otherwise provided. In this example, each of the leaf nodes provided contain at least K descendent species. Also, each node containing more than the maximum number S descendent species may be divided or split into smaller nodes (ie., finer-grain nodes).

Returning to FIG. 6, in STEP 605, event rates may be determined based on, for example, event counts, sequence counts, and/or species counts for any node or sequence. In one example, a phylogenetic or evolutionary tree may be pruned (STEP 604) such that the tree may contain K leaf nodes. Each of the K leaf nodes in the pruned tree may have a corresponding event count and/or sequence count for each position as described. The event rate may be determined in a variety of ways. For example, the even count at a position in a sequence of a biomolecule may be used to determine the event rate for the position of the molecule. In this example, the event rate may be represented as follows:

$$\text{Event\_rate} = \frac{\text{Event\_Count}}{\text{Sequence\_Count\_of\_descendent\_sequences}}$$

Alternatively, the event rate may be based on a number of species with a position of interest populated. In this example, the event rate may be represented as follows:

$$\text{Event\_rate} = \frac{\text{Event\_Count}}{\text{Descendent\_species\_with\_position\_populated}}$$

In STEP 606, a vector may be generated. In this example, a vector of any number of components may be generated for representing any position in a sequence of any node. For example, the vector V may be generated for each position or monomer in a sequence and may include components in which each component k of vector V corresponds to the event rate for the kth leaf node in a pruned phylogenetic or evolutionary tree. Alternatively or additionally, each position or monomer in a sequence may contain an additional k+1 component in a corresponding vector V representing an overall event rate from the root node.

Clusters of related sequences or biomolecules may be identified based on the vectors. For example, any of the generated vectors may be clustered to identify groupings or clusters of amino acid or nucleotide positions that are likely to be related (STEP 607). Clustering data may include any number of steps including, for example, normalizing any number of components in any of the vectors. The normalization of the components may be based on, for example, a mean and/or standard deviation of a value of a component across all column positions. In this example, each of the values of a corresponding identified position may be observed. A mean and/or standard deviation may be calculated for each of the values of the corresponding identified position and may further be normalized. Based on the normalized components of any of the generated vectors, groups of positions in the sequences or biomolecules may be identified as sharing similar phylogenetic patterns of event rate variation. Also, based on similarities of phylogenetic patterns of event rate variation of the positions in the groups of positions, other relationships may be identified among the positions in the groups. These may include any number or type of relationships including, but not limited to, structural and/or functional relationships.

Clustering of the data may be accomplished in a variety of ways. In one example, K-Means clustering may be applied to any of the vectors or components of the vectors to obtain groupings or clusterings of positions of interest. Alternatively or additionally, other clustering techniques may be employed such as, for example, Agglomerative Hierarchical Clustering.

In one example to illustrate, a large cluster may be identified that includes a large number of positions of sequences. The positions within the identified large cluster may be associated with a low event rate across various nodes or across all nodes. In this case, the large cluster or group may be identified as containing a highly conserved structure (i.e., low event rate across nodes). Also, in Agglomerative Hierarchical Clustering, a range of thresholds may be employed to identify varying levels of similarity of vectors associated with positions. In this example, hierarchical clusters may be identified containing groups of positions of different threshold similarities.

In another example (e.g., Agglomerative Hierarchical Clustering), positions whose vectors appear as closest "neighbors" within the cluster model may be strong candidates for interacting—for example as a base pair in an RNA helix secondary structure. Such positions may participate in forming a conserved structure even if their vectors show high event counts in some nodes. Positions whose vectors are located "nearby" in a clustering model in this example may be identified as a secondary group of positions. The secondary group of positions may further be identified as a set positions of relevance in a biomolecule. Similarly, using other methods such as K-Means Clustering, clusters of positions are determined that show different event rates in different nodes—but similar patterns of node-based event rate variation within each cluster. Such clusters may be identified as a set of positions of relevance in a biomolecule. Positions in an identified cluster may further be projected into a schematic or a model of a structure of a corresponding molecule. The model or schematic may provide additional information such as spatial location or relative positioning of the different positions within the molecule. In this case, positions identified as located spatially within a threshold distance of other positions may be identified as potentially within a similar or same cluster or group of positions. The cluster or group of positions may further be identified as related positions.

Hence, similar positions in a sequence of a molecule may be identified based on an event count, sequence count, species count and/or event rate corresponding to each position in a sequence of nodes in a phylogenetic or evolutionary tree. Parameters for any position may be compared with parameters for any other position which may further be accomplished by generating a vector for each of the positions. Components of each of the vectors may be analyzed for similarity with components of any other vector for any other position in a sequence of a biomolecule. For example, the components of the vectors may be used to cluster positions into groups or clusters of similar positions. Such clustering may be performed either by such computation or visually. If clustering is performed visually, the positions may be projected onto a schematic or model of the structure of the corresponding molecule. Relative positioning and spatial relationships of the positions may provide information on similarity or proximity of the positions of interest.

It is understood that aspects of the present description can take many forms and embodiments. The embodiments shown herein are intended to illustrate rather than to limit the description, it being appreciated that variations may be made without departing from the spirit of the scope of the invention. Although illustrative embodiments have been shown and described, a wide range of modification, change and substitution is intended in the foregoing disclosure and in some instances some features may be employed without a corresponding use of the other features. Accordingly, it is appropriate that the appended claims be construed broadly and in a manner consistent with the scope of the description.

The invention claimed is:

1. A method of identifying related positions in a set of biomolecular sequences, comprising:
   receiving a plurality of sequences of biomolecules, each sequence comprising monomers and corresponding to one or more species;
   aligning the sequences to generate aligned sequences;
   mapping the aligned sequences to an evolutionary tree, such that each leaf node of the tree corresponds to one or more of the sequences;
   selecting a position in the aligned sequences;
   counting evolutionary events in the selected position, such that each node of the evolutionary tree corresponds to an evolutionary event count for the selected position, the evolutionary event count of each node being the number of times that the identity of a monomer at that position changes in the children of that node;
   pruning the evolutionary tree;

generating a vector for the selected position, the vector comprising the evolutionary event counts of all leaf nodes in the pruned tree;

repeating the selecting a position, the counting evolutionary events in the selected position, the pruning the evolutionary tree, and the generating a vector for the selected position, for at least one other selected position;

clustering the generated vectors, thereby identifying related positions in the plurality of sequences;

wherein at least one of the aligning the sequences, the mapping the aligned sequences, the selecting a position, the counting evolutionary events, the pruning the evolutionary tree, and the clustering the generated vectors is performed by a computing device.

2. The method of claim 1, wherein the pruning the evolutionary tree further comprises discarding one or more nodes from the evolutionary tree.

3. The method of claim 2, wherein the discarding one or more nodes from the evolutionary tree further comprises counting the number of species to which each node and its children correspond, and discarding at least one node for which the species count is less than a threshold value.

4. The method of claim 1, wherein the pruning the evolutionary tree further comprises combining a plurality of sibling nodes.

5. The method of claim 4, wherein the combining a plurality of sibling nodes further comprises counting the number of species to which each node and its children correspond, and combining two or more nodes to yield a combination node for which the species count is greater than a threshold value.

6. The method of claim 1, wherein the pruning the evolutionary tree further comprises splitting one or more nodes.

7. The method of claim 6, wherein the splitting one or more nodes further comprises counting the number of species to which each node and its children correspond, and splitting one or more nodes for which the species count is greater than a threshold value.

8. The method of claim 1, wherein the generating a vector further comprises dividing each evolutionary event count by:
the number of sequences to which the node corresponds,
the number of sequences to which the node corresponds that have a monomer at the selected position,
the number of sequences to which the node and its children correspond that have a monomer at the selected position,
the number of species to which the node corresponds, or
the number of species to which the node and its children correspond.

9. The method of claim 1, wherein the vectors generated for the selected positions further comprise the evolutionary event count of the root of the evolutionary tree.

10. The method of claim 1, wherein the clustering the generated vectors further comprises normalizing the values of the vector components of the generated vectors.

11. The method of claim 1, wherein the clustering the generated vectors is performed by k-means clustering or agglomerative hierarchical clustering.

12. One or more computer-readable storage media storing computer-executable instructions that, when executed, cause one or more processors to perform a method of identifying related positions in a set of biomolecular sequences comprising:

receiving a plurality of sequences of biomolecules, each sequence comprising monomers and corresponding to one or more species;

aligning the sequences to generate aligned sequences;

mapping the aligned sequences to an evolutionary tree, such that each leaf node of the tree corresponds to one or more of the sequences;

selecting a position in the aligned sequences;

counting evolutionary events in the selected position, such that each node of the evolutionary tree corresponds to an evolutionary event count for the selected position, the evolutionary event count of each node being the number of times that the identity of a monomer at that position changes in the children of that node;

pruning the evolutionary tree;

generating a vector for the selected position, the vector comprising the evolutionary event counts of all leaf nodes in the pruned tree;

repeating selecting a position, counting evolutionary events in the selected position, pruning the evolutionary tree, and generating a vector for the selected position, for at least one other selected position;

clustering the generated vectors, thereby identifying related positions in the plurality of sequences.

13. The one or more computer-readable storage media of claim 12, wherein the instructions for pruning the evolutionary tree further comprise instructions for discarding one or more nodes from the evolutionary tree.

14. The one or more computer-readable storage media of claim 13, wherein the instructions for discarding one or more nodes from the evolutionary tree further comprise instructions for counting the number of species to which each node and its children correspond, and discarding the nodes for which the species count is less than a threshold value.

15. The one or more computer-readable storage media of claim 14, wherein the instructions for pruning the evolutionary tree further comprise instructions for combining a plurality of sibling nodes.

16. The one or more computer-readable storage media of claim 15, wherein the instructions for combining the plurality of sibling nodes further comprise instructions for counting the number of species to which each node and its children correspond, and combining two or more nodes to yield a combination node for which the species count is greater than a threshold value.

17. The one or more computer-readable storage media of claim 12, wherein the instructions for pruning the evolutionary tree further comprise instructions for splitting one or more nodes.

18. The one or more computer-readable storage media of claim 17, wherein the instructions for splitting one or more nodes further comprise instructions for counting the number of species to which each node and its children correspond, and splitting the one or more nodes for which the species count is greater than a threshold value.

19. The one or more computer-readable storage media of claim 12, wherein the instructions for generating a vector further comprise instructions for dividing each evolutionary event count by:
the number of sequences to which the node corresponds,
the number of sequences to which the node corresponds that have a monomer at the selected position,
the number of sequences to which the node and its children correspond that have a monomer at the selected position,
the number of species to which the sequences of the node correspond, or
the number of species to which the sequences of the node and its children correspond.

20. The one or more computer-readable storage media of claim 12, wherein the vectors generated for the selected positions further comprise the evolutionary event count of the root of the evolutionary tree.

21. The one or more computer-readable storage media of claim 12, wherein the instructions for clustering the generated vectors further comprise instructions for normalizing the values of the vector components of the generated vectors.

22. The one or more computer-readable storage media of claim 12, wherein the instructions for clustering the generated vectors perform the clustering by k-means clustering or agglomerative hierarchical clustering.

23. A system comprising:
one or more processors; and
memory storing components that, when executed, cause the one or more processors to perform a method of identifying related positions in a set of biomolecular sequences comprising:
receiving a plurality of sequences of biomolecules, each sequence comprising monomers and corresponding to one or more species;
aligning the sequences to generate aligned sequences;
mapping the aligned sequences to an evolutionary tree, such that each leaf node of the tree corresponds to one or more of the sequences;
selecting a position in the aligned sequences;
counting evolutionary events in the selected position, such that each node of the evolutionary tree corresponds to an evolutionary event count for the selected position, the evolutionary event count of each node being the number of times that the identity of a monomer at that position changes in the children of that node;
pruning the evolutionary tree;
generating a vector for the selected position, the vector comprising the evolutionary event counts of all leaf nodes in the pruned tree;
repeating selecting a position, counting evolutionary events in the selected position, pruning the evolutionary tree, and generating a vector for the selected position, for at least one other selected position;
clustering the generated vectors, thereby identifying related positions in the plurality of sequences.

24. The system of claim 23, wherein the generating a vector further comprises dividing each evolutionary event count by:
the number of sequences to which the node corresponds,
the number of sequences to which the node corresponds that have a monomer at the selected position,
the number of sequences to which the node and its children correspond that have a monomer at the selected position,
the number of species to which the sequences of the node correspond, or
the number of species to which the sequences of the node and its children correspond.

25. The method of claim 23, wherein the vectors generated for the selected positions further comprise the evolutionary event count of the root of the evolutionary tree.

* * * * *